United States Patent [19]
Heindl et al.

[11] Patent Number: 6,107,036
[45] Date of Patent: Aug. 22, 2000

[54] HETEROCYCLIC DIOXETHANE SUBSTRATES, PROCESS FOR THEIR PREPARATION AND THEIR USE

[75] Inventors: Dieter Heindl, München; Hans-Peter Josel, Weilheim; Herbert Von Der Eltz, Weilheim; Rupert Herrmann, Weilheim; Hans-Joachim Höltke, Penzberg; Rainer Beckert, Jena-Wogau; Dieter Weiss, Jena; Waldemar Adam, Würzburg, all of Germany

[73] Assignee: Roche Diagnostics GmbH, Mannheim, Germany

[21] Appl. No.: 09/051,487

[22] PCT Filed: Oct. 17, 1996

[86] PCT No.: PCT/EP96/04506

§ 371 Date: Apr. 20, 1998

§ 102(e) Date: Apr. 20, 1998

[87] PCT Pub. No.: WO97/14696

PCT Pub. Date: Apr. 24, 1997

[30] Foreign Application Priority Data

Oct. 18, 1995 [DE] Germany .................. 195 38 708

[51] Int. Cl.[7] .................. C12Q 1/68; C12Q 1/44; C07J 21/00; C07D 263/52; C07D 305/00
[52] U.S. Cl. .................. 435/6; 435/19; 540/31; 548/216; 549/214; 549/221; 549/334
[58] Field of Search .................. 435/6, 19; 549/214, 549/221, 334; 540/31; 548/216

[56] References Cited

U.S. PATENT DOCUMENTS

| | | | |
|---|---|---|---|
| 5,770,743 | 6/1998 | Schaap et al. | 548/526 |
| 5,773,628 | 6/1998 | Akhavan-Tafti et al. | 549/221 |
| 5,929,254 | 7/1999 | Matsumoto et al. | 549/214 |

*Primary Examiner*—Deborah C. Lambkin

*Attorney, Agent, or Firm*—Arent Fox Kintner Plotkin & Kahn PLLC

[57] ABSTRACT

Compounds of the general formula Ia and Ib are described

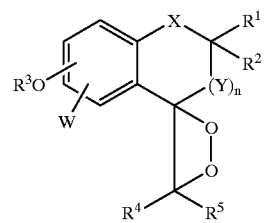

(Ia)

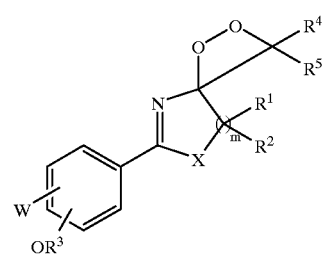

(Ib)

in which $R^1$ and $R^2$ are the same or different and represent hydrogen, straight-chain or branched $C_1$ to $C_6$ lower alkyl or an aryl group optionally substituted by electron-withdrawing groups, $R^3$ denotes a cleavable group, W is hydrogen, halogen or a pseudohalogen and at least one of the groups $R^4$ or $R^5$ is a group stabilizing the dioxetane structure and at most one of the groups $R^4$ or $R^5$ represents hydrogen and X or Y represents oxygen, N-R or $C(R)_2$ in which R has the meanings stated for $R^1$ and $R^2$ or represents a mesomeric double bond or a carbonyl group and n denotes the number 0 or 1 and m denotes the number 1 or 2, as well as a process for their production. These compounds are new and can be used as substrates in immunological assays and in DNA diagnostics using activating agents for colour formation.

13 Claims, No Drawings

HETEROCYCLIC DIOXETHANE SUBSTRATES, PROCESS FOR THEIR PREPARATION AND THEIR USE

This application is a 371 of PCT/EP96/04506 Oct. 17, 1996.

The invention concerns heterocyclic dioxetane substrates, processes for their production and their use in enzymatic analytical methods.

It has been known for a long time that oxiluciferin is formed by the reaction of luciferin with luciferase, oxygen and ATP. In this reaction light (wavelength maximum at 562 nm) is emitted as chemiluminescence. In this process a dioxetane is presumably formed as an energy-rich intermediate product (F. McCapra, Chem. Commun. 155 (1968)). Numerous chemiluminescent 1,2-dioxetane compounds have been developed based on this postulate.

The adamantyl residue has been described for the stabilization of the unstable 1,2-dioxetanes (EP-A 0 254 051, EP-A 0 352 713, WO 91/03479, WO 90/07511, WO 92/04341 as well as publications cited therein). The chemiluminescence yield then develops with the decay of the dioxetanes and is dependent among others on the fluorescent properties of the emitter formed. Although the phenolates that are formed on decay of the dioxetane derivatives that are usually used (3-(2'-spiro-adamantane)-4-methoxy-4-(3"-phosphoryloxy)phenyl-1,2-dioxetane or corresponding dioxetanes halogenated on the adamantyl residue) have a good fluorescence quantum yield, the substrates have an overall low chemiluminescence. Dioxetanes with improved chemiluminescence yields would be particularly desirable in the triggered decay of dioxetanes.

Stabilized dioxetane derivatives are known from WO 93/20083 which decay into oxyluciferin and phenylthiazoline derivatives as emitters. Although these dioxetanes decay with a higher light yield than other known dioxetanes, they are very difficult to prepare synthetically.

Hence the object of the present invention was to provide new 1,2-dioxetanes which are stable and which only decay by reaction with an activating agent with the formation of a high light yield and which can be prepared by relatively simple chemical synthesis. This object is achieved by a compound of the general formula Ia or Ib

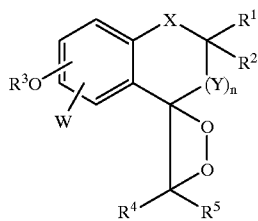
(Ia)

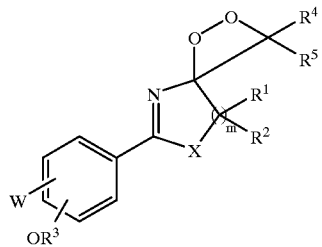
(Ib)

in which

R$^1$ and R$^2$ are each the same or different and represent hydrogen, straight-chain or branched C$_1$ to C$_6$ lower alkyl, individually or together a 3-6 carbon atom cycloalkyl or an aryl group (preferably phenyl or naphthly with optionally one or several substituted electron-withdrawing groups provided that only one of the residues R$^1$ or R$^2$ is hydrogen, m denotes the number 1 or 2, R$^3$ is a cleavable group which can be cleaved off by an activating agent, W is hydrogen, halogen or a pseudohalogen such as rhodanide or cyanide residues and is preferably in the ortho position relative to the O-R$^3$ group, at least one of the groups R$^4$ or R$^5$ is a group stabilizing the dioxetane structure and at most one of the groups R$^4$ or R$^5$ represents hydrogen, and X and Y represent oxygen, N-R or C(R)$_2$ in which R has the stated meanings for R$^1$ and R$^2$ or it is a double bond in a mesomeric system or it represents a carbonyl group and n denotes the number 0 or 1.

Acids, bases, salts, enzymes, inorganic or organic catalysts and electron donors are preferably used as activating agents.

The group O-R$^3$ can be located at any position of the phenyl ring. If X is oxygen, the group O-R$^3$ is preferably located in the 5-position in the case of compounds of the general formula Ia and where n is 0, in the case of Ib and where m equals 1 it is preferably in the 3-position and in the case of Ib and where m equals 2 it is preferably in the 4-position.

The group O-R$^3$ is preferably a hydroxy salt or an oxy acid, phosphate, arylcarboxyl ester or alkylcarboxyl ester, alkyloxy, alkylsilyloxy or arylsiloxy, sulfate, oxypyranoside or a glyceridyl or phosphoryl residue or a steroid derivative. Phosphate and a dimethyl-tertiary butyl-silyloxy group are particularly preferred for O-R$^3$.

The composition of the aryl and alkyl residues is not critical. Preferred aryl in this application are phenyl and naphthyl, and preferred alkyl residues are C$_1$–C$_6$, unless otherwise noted. Any person skilled in the art can select suitable residues for R$^3$ without difficulty. The only requirements are solubility and cleavability of R$^3$ by the activating agents. Any reagent which is capable of removing the R$^3$ group, and therefore provide an activated phenoxide ion which decomposes with light emission can be used as the activating agent. The particular type of the reagent depends upon the nature of the R$^3$ group; e.g. if R$^3$ is hydrogen, the reagent is a base; if SiR$_3$, the reagent is a fluoride anion; if R$^3$ is PO$^-_3$, the reagent is a phosphatase enzyme, and so on.

Hydrogen, methyl, ethyl or phenyl groups are preferred for R$^1$ and R$^2$, or if R$^1$ and R$^2$ together denote a phenylene group with (C)$_m$ and m equals 2 whereby the phenyl and phenylene groups can for example be substituted by a halogen residue. If for example phosphate is used as O-R$^3$, the chemiluminescence reaction can be induced by adding alkaline phosphatase. If a galactoside is used the chemiluminescence reaction can be induced by β-galactosidase. If a silyloxy residue is used as O-R$^3$, the chemiluminescence can be induced by adding fluoride.

Suitable groups R$^4$ and/or R$^5$ that stabilize the dioxetane structure are groups which protect the dioxetane group from uncontrolled conversion. This stabilization is preferably achieved by steric shielding of this group. Hence condensed aliphatic or aromatic ring systems which can optionally be substituted by electron withdrawing groups come into particular consideration for this purpose. Preferred systems are 2- to 5-membered cycloalkyl with 3–6 carbon atoms; preferably at least one of the members is an aromatic ring.

Carbonyl or halogen can for example be used as electron withdrawing groups. However, all groups with a positive $\sigma_p$ value can be used (See March, Advanced Organic Chemistry, Wiley Interscience 1992, 4th Ed. p. 280). Preferred groups in this regard are halogen, cyano and RCO groups where R is $C_1$–$C_6$ alkyl. Adamantanyl, phenyl, cyclohexyl, secondary and tertiary aliphatic alkyl groups (such as e.g. the t-butyl group) in a substituted and unsubstituted form are also suitable. In this case $R^4$ and $R^5$ can be the same or different. In the case of phenyl and/or cyclohexyl groups, individual residues as well as in the form of condensed ring systems come into consideration as substituents which can optionally have further structural units such as e.g. a cyclopentyl residue as in steroids. Corresponding residues are summarized within the scope of the present invention as polycycloalkyl and polycycloaryl residues. In the case of the adamantyl residue or for example a steroidyl residue, this is preferably bound in such a way that $R^4$ and $R^5$ denote parts of the ring structure and are consequently bridged (formulae Ia' and Ia"):

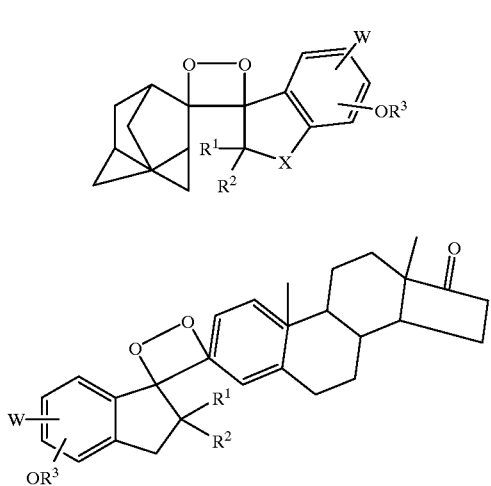

Appropriate steriod derivatives for $R^4$ and $R^5$ are as follows:

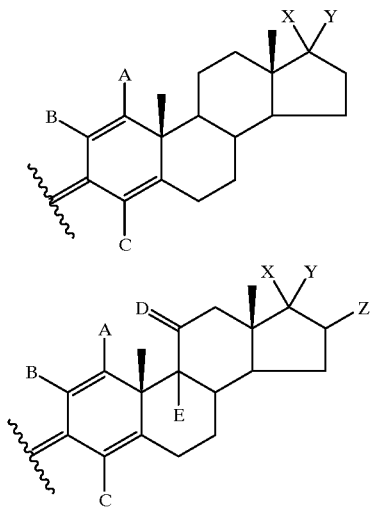

in which each of A, B, C is H; A or B is halogen; A or C is methyl; each of X, Y can be H, =O, =CHO₂Et, CH(Me)CH₂OAc, CH(Me)CO₂Me, OAc, C=CH CH(Me)CH₂OH, CH(Me)CO₂H, OH, COCH₂OAc, OCH(Me)CH₂OEt or both together are OCH₂OCH₂O, N—OH, NNHPh, NNMe₂, NNHCSNH₂ or NNHCONH₂; D is OH or a protected OH or =O; E is halogen, e.g. fluor, chlor; and Z can be alkyl consisting of 1 to 10 C atoms. See also, D. Weiss et al., Synthesis, August 1992, p. 751–752, hereby incorporated by reference.

According to the invention the dioxetanes of benzofuranes have proven to be particularly suitable:

3-(7'-t.-butyldimethylsilyloxy-2',2'-dimethylbenzofuran-3'-yl)-4-spiro-(tricyclo[3.3.1.1.³,⁷]yl)-1,2-dioxetane, the disodium salt of 3-(7'-phosphoryl- 2',2'-dimethyl-benzofuran-3'-yl)-4-spiro-(tricyclo [3.3.1.1.³,⁷]yl)-1,2-dioxetane, 3-(7'-t.-butyl-dimethylsilyloxy-2',2'-dimethyl-benzofuran-3'-yl)-4-spiro-(5"-chloro-tricyclo[3.3.1.1.³,⁷] yl)-1,2-dioxetane, the disodium salt of 3-(7'-phosphoryl-2',2'-dimethyl-benzofuran-3'-yl)-4-spiro-(5"-chloro-tricyclo [3.3.1.1.³,⁷]-yl)-1,2-dioxetane, 3-(5'-t.-butyldimethylsilyloxy-2',2'-dimethyl-benzofuran-3'-yl)-4-spiro-(5"-chloro-tricyclo[3.3.1.1.³,⁷]yl)-1,2-dioxetane, the disodium salt of 3-(5'-phosphoryl-2',2'-dimethyl-benzofuran-3'-yl)-4-spiro-(5"-chloro-tricyclo [3.3.1.1.³,⁷] yl)-1,2-dioxetane, 3-(5'-t.-butyldimethylsilyloxy-6'-chloro-2',2'-dimethyl-benzofuran-3'-yl)-4-spiro-(5"-chloro-tricyclo[3.3.1.1.³,⁷]yl)-1,2-dioxetane, the disodium salt of 3-(5'-phosphoryl-6'-chloro-2',2'-dimethyl-benzofuran-3'-yl)-4-spiro-(5"-chloro-tricyclo [3.3.1.1.³,⁷]yl)-1,2-dioxetane, (4'Ξ)-5"-t.-butyldimethylsilyloxy-6"-chloro-2",2"-dimethyl-17-oxo-(3ζO)-dispiro[androsta-1,4-diene-3,3'-[1,2]dioxetane-4', 3"-benzofurane or (4Ξ)-6"-chloro-2",2"-dimethyl-17-oxo-(3ξ)-dispiro[androsta-1,4-diene-3,3'-[1,2]dioxetane-4',3"-benzofuran-5"-yl disodium phosphate.

The compounds of the general formulae Ia and Ib are new. A process for synthesizing these compounds has not been known previously.

Hence a subject matter of the invention is also a process for the production of the compounds of the general formulae Ia and Ib, which is characterized in that heterocyclic carbonyl compounds of the general formulae II, III or IV

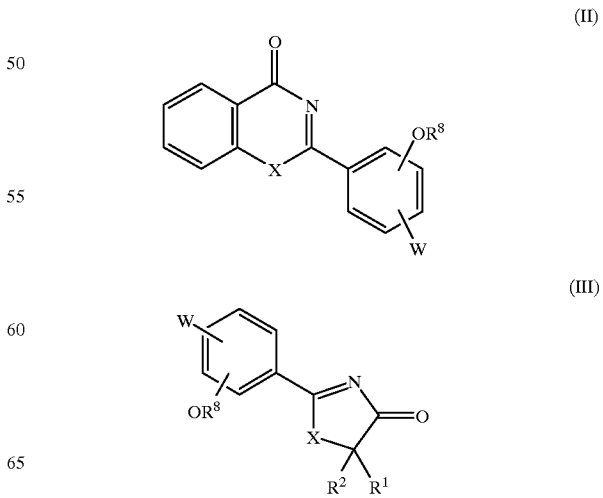

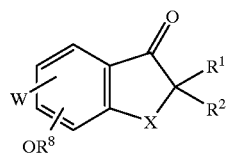

(IV)

in which
R[8] represents a straight-chain or branched alkyl residue with 1 to 6 C atoms, preferably a methyl residue or a hydrogen atom, W represents a halogen or pseudohalogen residue such as for example SCN or CN or represents a hydrogen atom, X represents oxygen or N-alkyl and the residues R[1] and R[2] have the meanings mentioned above are reacted with a compound of the general formula (V),

(V)

in which R[4] and R[5] have the above-mentioned meanings, with the exclusion of water and air in the presence of titanium trichloride and a reducing agent, if R[8] is alkyl, the reaction product is dealkylated in the presence of for example boron triiodide or sodium ethanethiolate, or if R[8] denotes hydrogen, the cleavable group R[3] is introduced directly according to a method familiar to a person skilled in the art and subsequently dioxygenated to form dioxetane.

The heterocyclic carbonyl compounds are produced according to methods described in the literature cf. e.g. Tetrahedron 1978, 34, 2035; Helv. Chim. Acta 1972, 55, 1567; J.Agric. Food. Chem. 1968, 300; J. Am. Chem. Soc. 1967, 87, 6527.

The reaction of the compounds II, III and IV with the compound V is carried out in a solvent that is as unpolar as possible, preferably tetrahydrofuran or dimethoxyethane, in the presence of titanium trichloride and a reducing agent, preferably zinc/copper or lithium aluminium hydride. Aldehydes and ketones that are especially suitable as compound V are those which have residues R[4] and R[5] that stabilize the final product the dioxetane. Such a stabilization can be achieved by steric shielding of the dioxetane structure. Hence suitable ketones and aldehydes are for example adamantanone, polycyclic ketones such as e.g. a steroid ketone, secondary and tertiary aliphatic ketones and aldehydes such as e.g. t.-butylketone. These ketones can carry further substituents preferably chlorine atoms.

In the case of compounds in which R[8] is an alkyl residue preferably methyl, it is expedient to carry out the dealkylation with a dealkylation agent preferably with boron triiodide or sodium ethanethiolate.

It is also possible to convert the heterocyclic ketones II, III and IV into the heterocyclic thiones of the general formulae VI, VII and VIII in which R[8] and W, X and R[1] and R[2] represent the above-mentioned substituents, and subsequently to react them with diazo compounds of the general formula IX in which R[4] and R[5] have the above-mentioned meanings. In the case that R[8] is methyl the alkenes that are formed are dealkylated according to the method described above. Subsequently the cleavable group R[3] is introduced as described above and the dioxygenation is carried out.

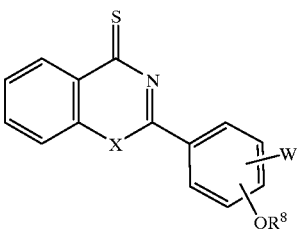

(VI)

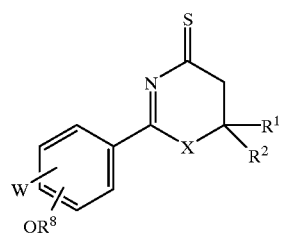

(VII)

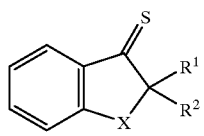

(III)

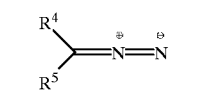

(IX)

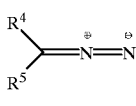

The carbonyl function is converted into a thiocarbonyl function by reacting the heterocyclic ketones with a sulfurization reagent, preferably Lawesson reagent (2,4-bis-(4-methoxyphenyl)-1,3-dithia-2,4-diphosphetane-2,4-disulfide) or phosphorus pentasulfide in toluene or pyridine.

The reaction with diazo components for example with di-tertiary butyldiazomethane or with a diazosteroid is preferably carried out in an unpolar solvent such as diethyl ether. The diazo component is produced by oxidation of hydrazones with an oxidizing agent preferably manganese dioxide or silver oxide. Diazo compounds are preferably suitable as compound IX which stabilize the dioxetane by means of the residues R[4] and R[5]. Such a stabilization can be achieved by steric shielding of the dioxetane structure. Hence suitable diazo compounds are for example diazoadamantane, chlorodiazoadamantane, diphenyldiazomethane, polycyclic diazo compounds such as e.g. a diazosteroid, secondary or tertiary aliphatic ketones and aldehydes such as e.g. di-tert.-butyl ketone. These diazo compounds can carry further substituents preferably chlorine atoms.

The cleavable chemically labile group is introduced by methods familiar to a person skilled in the art. Such methods are for example described in Houben Weyl XII/2.

It is expedient to carry out the dioxygenation by reacting the alkene which is either dissolved in methylene chloride or in methanol at a temperature of about −30 to −10° C. with singlet oxygen which is formed in situ by irradiation with visible light using a sensitizer (Rose Bengal, methylene blue, cf.Tetrahedron Letters 1988, 3137–3140).

The purification is carried out in particular by filtration or other methods familiar to a person skilled in the art.

A further subject matter of the invention is a method for the determination of an acid, base, a salt, enzyme, inorganic or organic catalyst and electron donors by reacting this compound with a compound of the general formula Ia or Ib and measuring the emitted light as a measure of the content of the compound to be determined.

This method is particularly preferably used to determine enzymes, especially marker enzymes, in immunological systems or for DNA diagnostics with labelled DNA probes. A detailed description of the method involved can be found in Kessler, Springer, Publ. Berlin 1992, in particular chapter 3.2.12, .13 and 19.6.

Alkaline phosphatase is preferably determined in which case the chemically labile group $R^3$ is phosphate or β-galactosidase in which case $R^3$ is a galactoside.

The invention is elucidated by the following examples:

EXAMPLE 1

2-(4'-Methoxyphenyl)-4H-1,3-benzoxazin-4-one 2.5 ml pyridine is added to a suspension of 0.25 mol salicylamide in 50 ml xylene. While boiling under reflux (water separator) 0.26 mol 4-methoxybenzoyl chloride is added within 3 hours and it is heated to boiling for a further 3 hours under reflux. A further 2.5 ml pyridine is added and it is heated for a further 8 hours. After cooling to room temperature it is poured onto 400 ml isopropanol and suction filtered. The residue is recrystallized from ethylene glycol monomethyl ether.

Yield 0.2 mol

EXAMPLE 2

4-Adamantylidene-2-(4'-methoxyphenyl)-4H-1,3-benzoxazine 21 mmol lithium aluminium hydride is carefully added to a suspension of 40 mmol titanium chloride in 100 ml absolute THF while stirring vigorously. After stirring for 1 hour at room temperature, a mixture of 15 mmol 2 -(4'-methoxyphenyl)-4H-1,3-benzoxazine-4-one and 11 mmol adamantanone is added while cooling on ice. It is heated to boiling for 60 min under reflux. After cooling to room temperature it is poured onto 200 ml water. The mixture is shaken out twice with 200 ml ethyl acetate each time. The combined organic phases are washed once with water and separated. After drying over sodium sulfate it is filtered and the solvent is removed by distillation. The oily residue is separated by column chromatography (silica gel: ethyl acetate/petroleum ether 1:9).

Yield 6 mmol

EXAMPLE 3

4-Adamantylidene-2-(4'-hydroxyphenyl)-4-H-1,3-benzoxazine

A solution of 6 mmol 4-adamantylidene-2-(4'-methoxyphenyl)-4H-1,3-benzoxazine in 20 ml absolute methylene chloride is added dropwise to a solution of 12 mmol boron triiodide while stirring at −25° C. with the exclusion of air and water. The mixture is heated to room temperature within one hour and stirred for a further 4 hours. After admixing with 50 ml water the organic phase is separated and dried over sodium sulfate. The solvent is removed by distillation. The oily residue is separated by column chromatography (silica gel: ethyl acetate/petroleum ether 1:3).

Yield 3.2 mmol

EXAMPLE 4

4-Adamantylidene-2-(4'-t.butyldimethylsilyloxyphenyl)-4H-1,3-benzoxazine 3 mmol 4-adamantylidene-2-(4'-hydroxyphenyl)-4H-1,3-benzoxazine is suspended in 30 ml absolute methylene chloride. 6 mmol imidazole and 6 mmol t.-butyldimethylsilyl chloride are added in succession. After stirring for 14 h at room temperature it is filtered. The filtrate is shaken out successively with 20 ml 1 M sodium hydroxide solution, 20 ml 2 M hydrochloric acid and 20 ml water each time. The separated organic phase is dried over sodium sulfate. The solvent is removed by distillation. The oily residue is recrystallized from a small amount of petroleum ether.

Yield 2.7 mmol

EXAMPLE 5

Disodium salt of 4-adamantylidene-2-(4'-phosphoryl-phenyl)-4H-1,3-benzoxazine

A solution of 3 mmol 4-adamantylidene-2-(4'-hydroxyphenyl)-4H-1,3-benzoxazine in a mixture of 3 ml acetone and 3 ml pyridine is added dropwise to a solution of 1.5 ml phosphoroxy chloride in 7.5 ml acetone while stirring at 0° C. It is stirred for 1 hour at 0° C. and subsequently poured onto 60 ml saturated saline solution and suction filtered. The residue is suspended in 1.5 ml water. A pH value of 10 is set with 2 M sodium hydroxide solution. It is admixed with 30 ml ethanol and suction filtered. The residue is dried in a vacuum.

Yield 2.2 mmol

EXAMPLE 6

3-[2'-(4"-t.butyldimethylsilyloxyphenyl)-4'H-1,3-benzoxazin-4'-yl]-4-spiroadamantyl-dioxetane 2 mmol 4-adamantylidene-2-(4'-t.butyldimethylsilyloxyphenyl)-4H-1,3-benzoxazine dissolved in 20 ml absolute methylene chloride is irradiated for 2 hours at −30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 2 mmol

EXAMPLE 7

Disodium salt of 3-[2'-(4"-phosphoryl-phenyl)-4'H-1,3-benzoxazin-4'-yl]-4-spiroadamantyl-dioxetane 2 mmol of the disodium salt of 4-adamantylidene-2-(4'-phosphoryl-phenyl)-4H-1,3-benzoxazine dissolved in 20 ml absolute methanol is irradiated for 2 hours at −30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 2 mmol

EXAMPLE 8

2-(3'-Methoxyphenyl)-5,5-dimethyl-oxazolin-4-one 50 mmol acetone is added at 0° C. to a solution of 57 mmol potassium cyanide in 50 ml water. 57 mmol 3-methoxybenzoyl chloride is added dropwise within 90 minutes at room temperature while stirring vigorously. After stirring for a further 90 min at 0° C. it is allowed to stand for 10 h at room temperature. It is admixed with 100 ml diethyl ether and the mixture was shaken out twice with 50 ml saturated sodium hydrogen carbonate solution each time and then with 100 ml water. The organic phase is separated and dried over sodium sulfate. The solvent is removed by distillation. The oily residue (6.6 g 3-methoxybenzoic acid-2'-cyanoisopropyl ester) is dried in a high vacuum and subsequently introduced into a mixture of 52 ml acetanhydride containing 10.4 ml 35% aqueous tetrafluoroboric acid. It is heated for 1 hour to boiling under reflux and after cooling to room temperature it is admixed with 300 ml ether. The precipitate that forms is suspended in 70 ml toluene. 70 mmol triethylamine is added to the suspension and it is stirred for 1 hour at room temperature. It is filtered. The filtrate is concentrated to dryness in a vacuum. The oily residue is separated by column chromatography (silica gel: ethyl acetate/petroleum ether 1:1).

Yield 17 mmol

EXAMPLE 9

4-Adamantylidene-2-(3'-methoxyphenyl)-5,5-dimethyl-oxazoline 122 mmol zinc-copper couple is added to a suspension of 35 mmol titanium trichloride in 60 ml absolute THF while stirring carefully. After heating for one hour under reflux a mixture of 11.4 mmol 2-(3'-methoxyphenyl)-5,5-dimethyl-oxazolin-4-one and 8.1 mmol adamantanone is added after cooling to room temperature. It is heated for 4 h to boiling at reflux. After cooling to room temperature it is poured onto 200 ml water. The mixture is shaken out twice with 200 ml ethyl acetate. The combined organic phases are washed once with water and separated. After drying over sodium sulfate it is filtered and the solvent is removed by distillation. The oily residue is separated by column chromatography (silica gel: ethyl acetate/petroleum ether 1:9).

Yield 7 mmol

EXAMPLE 10

4-Adamantylidene-2-(3'-hydroxyphenyl)-5,5-dimethyl-oxazoline

A solution of 7 mmol 4-adamantylidene-2-(3'-methoxyphenyl)-5,5-dimethyl-oxazoline in 20 ml absolute methylene chloride is added dropwise to a solution of 14 mmol boron triiodide while stirring at −25° C. with the exclusion of air and water. The mixture is heated to room temperature within one hour and stirred for a further 4 h. After admixing with 50 ml water the organic phase is separated and dried over sodium sulfate. The solvent is removed by distillation. The oily residue is separated by column chromatography (silica gel: ethyl acetate/petroleum ether 1:3).

Yield 3.9 mmol

EXAMPLE 11

4-Adamantylidene-2-(3'-t.butyldimethylsilyloxyphenyl)-5,5-dimethyl-oxazoline 3 mmol 4-adamantylidene-2-(3'-hydroxyphenyl)-5,5-dimethyl-oxazoline is suspended in 30 ml absolute methylene chloride. 6 mmol imidazole and 6 mmol t.-butyldimethylsilyl chloride are added successively. After stirring for 14 h at room temperature it is filtered. The filtrate is successively shaken out with 20 ml 1 M sodium hydroxide solution, 20 ml 2 M hydrochloric acid and 20 ml water each time. The separated organic phase is dried over sodium sulfate. The solvent is removed by distillation. The oily residue is separated by column chromatography (silica gel: petroleum ether).

Yield 2.5 mmol

EXAMPLE 12

Disodium salt of 4-adamantylidene-2-(3'phosphorylphenyl)-5,5-dimethyl-oxazoline

A solution of 3 mmol 4-adamantylidene-2-(3'-hydroxyphenyl)-5,5-dimethyl-oxazoline in a mixture of 3 ml acetone and 3 ml pyridine is added dropwise to a solution of 1.5 ml phosphoroxy chloride in 7.5 ml acetone while stirring at 0° C. It is stirred for 1 h at 0° C. and subsequently poured onto 60 ml saturated saline solution and suction filtered. The residue is suspended in 1.5 ml water. A pH value of 10 is set using 2 M sodium hydroxide solution. It is admixed with 30 ml ethanol and aspirated. The residue is dried in a vacuum.

Yield 2.0 mmol

EXAMPLE 13

3-[2'-(3"-t.butyldimethylsilyloxyphenyl)-5',5'-dimethyl-oxazoline-4'-yl]-4-spiroadamantyl-dioxetane 2 mmol 4-adamantylidene-2-(3I-t.-butyldimethylsilyloxyphenyl)-5,5-dimethyl-oxazoline dissolved in 20 ml absolute methylene chloride is irradiated for 2 h at −30° C. with a 1000 watt sodium-vapour lamp in the presence of 0.01% immobilized Rose Bengal while passing in dry oxygen. The reaction proceeds quantitatively. The sensitizer can be removed by filtration. The filtrate contains the dioxetane.

Yield 2 mmol

EXAMPLE 14

Disodium salt of 3-[2'-(3"phosphorylphenyl)-5', 5'-dimethyl-oxazoline-4'-yl]-4-spiroadamantyl-dioxetane 2 mmol disodium salt of 4-adamantylidene-2-(3'phosphorylphenyl)-5,5-dimethyl-oxazoline dissolved in 20 ml absolute methanol is irradiated for 2 hours at −30° C. with a 1000 watt sodium-vapour lamp in the presence of 0.01% immobilized Rose Bengal while passing in dry oxygen. The reaction proceeds quantitatively. The sensitizer can be removed by filtration. The filtrate contains the dioxetane.

Yield 2 mmol

EXAMPLE 15

7-Hydroxy-2,2-dimethyl-benzofuran-3-one

7-Hydroxy-2,3-dihydro-2,2-dimethylbenzofurane is dissolved in 100 ml pyridine. 0.5 mol benzoyl chloride is added dropwise at 0° C. within 4 h. Subsequently it is stirred for 10 h at room temperature. It is poured onto 200 ml ice water and aspirated. The residue is washed with 500 ml 2 M hydrochloric acid and then with 1000 ml water and dried in air. A solution of 0.906 mol chromium trioxide in 370 ml glacial acetic acid is added dropwise to a solution of this crude product (0.45 mol) in 600 ml glacial acetic acid in such a way that the temperature of the mixture does not exceed 20° C. After the dropwise addition is completed it is stirred for a further 1 hour at 40° C. and subsequently poured onto 2 l water. It is suction filtered. The residue is washed with 1 l water and recrystallized from ethanol/water 3:1. The benzoyl compound is fed into 400 ml 10% ethanolic potassium hydroxide solution and the mixture is heated for 1 hour to 70° C. It is admixed with 3 l water and suction filtered. The residue is recrystallized from 2 l water.

Yield 0.16 mol

EXAMPLE 16

3-(5'-Chloro-tricyclo[3.3.1.1.3.7]yl)-7-hydroxy-2,2-dimethyl-benzofurane 550 mmol zinc-copper-couple is carefully added to a suspension of 158 mmol titanium trichloride in 120 ml absolute THF while stirring vigorously. After heating for 1 hour under reflux, a mixture of 52 mmol 7-hydroxy-2,2-dimethyl-benzofuran-3-one and 37 mmol 5-chloro-adamantan-2-one is added at room temperature. It is heated for 30 min under reflux to boiling. After cooling to room temperature it is poured onto 200 ml water. The mixture is shaken out twice with 200 ml ethyl acetate each time. The combined organic phases are washed once with water and separated. After drying over sodium sulfate it is filtered and the solvent is removed by distillation. The oily residue is separated by column chromatography (silica gel: ethyl acetate/petroleum ether 1:9).

Yield 30 mmol

EXAMPLE 17

3-(5'-chloro-tricyclo[$3.3.1.1.^{3,7}$]-7-t.-butyldimethylsilyloxy-2,2-dimethyl-benzofurane 30 mmol 3-(5'-chloro-tricyclo[$3.3.1.1.^{3,7}$]yl)-7-hydroxy-2,2-dimethyl-benzofurane is suspended in 30 ml absolute methylene chloride. 60 mmol imidazole and 60 mmol t.-butyldimethylsilyl chloride are added in succession. After stirring for 14 h at room temperature it is filtered. The filtrate is shaken out successively with 100 ml 1 M sodium hydroxide solution, 100 ml 1 M hydrochloric acid and 20 ml water in each case. The separated organic phase is dried over sodium sulfate. The solvent is removed by distillation. The oily residue is separated by column chromatography (silica gel: petroleum ether).

Yield 27 mmol

EXAMPLE 18

Disodium salt of 3-(5'-chloro-tricyclo[$3.3.1.1.^{3,7}$]yl)-7-phosphoryl-2,2-dimethyl-benzofurane A solution of 30 mmol 3-(5'-chloro-tricyclo[$3.3.1.1.^{3,7}$]yl)-7-hydroxy-2,2-dimethyl-benzofurane in a mixture of 30 ml acetone and 30 ml pyridine is added dropwise at 0° C. to a solution of 15 ml phosphoroxy chloride in 75 ml acetone while stirring. It is stirred for 1 hour at 0° C. and subsequently poured onto 600 ml saturated saline solution and suction filtered. The residue is suspended in 15 ml water. A pH of 10 is set using 2 M sodium hydroxide solution. It is admixed with 300 ml ethanol and suction filtered. The residue is dried in a vacuum.

Yield 23 mmol

EXAMPLE 19

3-(7'-t.-butyldimethylsilyloxy-2',2'-dimethyl-benzofuran-3'-yl)-4-spiro-(5"-chloro-tricyclo [$3.3.1.1.^{3,7}$]yl)-1,2-dioxetane 10 mmol 3-(5'-chloro-tricyclo[$3.3.1.1.^{3,7}$]yl)-7-t.-butyldimethylsilyloxy-2,2-dimethyl-benzofurane dissolved in 200 ml absolute methylene chloride is irradiated for 2 hours at −30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 20 mmol

EXAMPLE 20

Disodium salt of 3-(7'-phosphoryl-2',2'-dimethyl-benzofuran-3'-yl)-4-spiro-(5"-chloro-tricyclo [$3.3.1.1.^{3,7}$]yl)-1,2-dioxetane 2 mmol disodium salt of 3-(5'-chloro-tricyclo [$3.3.1.1.^{3,7}$]yl)-7-phosphoryl-2,2-dimethyl-benzofurane dissolved in 20 ml absolute methanol is irradiated for 2 hours at −30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 2 mmol

EXAMPLE 21

5-Hydroxy-2,2-dimethyl-benzofuran-3-one 80 mmol t-butylhydroquinone together with 80 mmol potassium bromate is suspended in 100 ml water. 20 drops 1 M sulfuric acid is added thereto while stirring. The reaction mixture is slowly heated to 80° C. while stirring. A clear orange solution of the quinone forms. When this is cooled to room temperature orange needles precipitate (t-butylbenzoquinone). These are dissolved in 400 ml ethanol while still wet. The solution is irradiated for 15 h at 5° C. with a 250 W sodium-vapour lamp (TLC control). The solvent is removed by distillation, the residue is washed with toluene/hexane 1:1. The remaining colourless crystalline residue (2-(2'-ethyl-2'-ethoxy-propyl)-hydroquinone) is fed into a mixture of 4 ml ethanol and 80 ml glacial acetic acid. 4 ml 40% aqueous tetrafluoroboric acid is added while stirring. The mixture is heated to 80° C. during which a clear solution forms. After cooling to room temperature it is poured onto 200 ml water and extracted with toluene. The organic phase is washed once with water and dried over potassium carbonate. After removing the solvent by distillation an oil remains (5-hydroxy-2,2-dimethyl-2,3-dihydro-benzofurane). The benzoylation, oxidation and saponification are carried out as described in example 15.

Yield 25 mmol

EXAMPLE 22

6-Chloro-5-hydroxy-2,2-dimethyl-benzofuran-3-one 25 mmol 7-Hydroxy-2,2-dimethyl-benzofuran-3-one and 30 g silica gel are stirred in 200 ml chloroform. A solution of 25 mmol N-chloro-diisopropylamine in 100 ml chloroform (prepared from diisopropylamine and aqueous sodium hypochlorite solution, extracted in chloroform, concentration determined iodometrically) is added dropwise. After stirring for 10 hours it is filtered and the filtrate is shaken out with water. The solution is dried over sodium sulfate. The solvent is removed by distillation at 300 mbar. The residue is separated by column chromatography (silica gel: ethyl acetate).

Yield 20 mmol

EXAMPLE 23

6-Chloro-5-hydroxy-2,2-dimethyl-benzofurane-3-thione

A solution of 20 mmol 6-chloro-5-hydroxy-2,2-dimethyl-benzofuran-3-one in 30 ml toluene is admixed with 10 mmol Lawesson's reagent and heated for 3 hours to boiling under reflux. After cooling to room temperature it is filtered on 50 g silica gel. The red fraction of the filtrate is collected. After removing the toluene by distillation a red oil remains.

Yield 17 mmol

EXAMPLE 24

3-((E/Z)-)-6-chloro-5-hydroxy-2,2-dimethyl-benzofuran-3-ylidene)-androsta-1,4-diene-17-one 1 mmol Androsta-1,4-diene-3,17-dione-3-hydrazone is fed while stirring at room temperature into a suspension of 1.5 g manganese dioxide and 1.5 g aluminium oxide in 20 ml ether which had been admixed with 10 drops of water. After stirring for 1 hour the etheric solution of the diazosteroid is removed by filtration. 1 mmol 6-chloro-5-hydroxy-2,2-dimethyl-benzofurane-3-thione is added in portions to the filtrate. After stirring for two hours the ether is removed by distillation and the residue is chromatographed on silica gel (ethyl acetate/petroleum ether 1:9). The weakly yellow coloured fractions are collected. After removing the solvent by distillation a light yellow crystalline residue remains.

Yield 0.7 mmol

EXAMPLE 25

3-((E/Z)-)-6-chloro-5-t-butyldimethylsilyloxy-2,2-dimethyl-benzofuran-3-ylidene)-androsta-1,4-diene-17-one 30 mmol 3-(androsta-1',4'-diene-17'-one-3'-ylidene)-6-chloro-5-hydroxy-2,2-dimethyl-benzofurane is suspended in 30 ml absolute methylene chloride. 60 mmol Imidazole and 60 mmol t.-butyldimethylsilyl chloride are added in succession. After stirring for 14 hours at room temperature it is filtered. The filtrate is successively shaken out with 100 ml 1 M sodium hydroxide solution, 100 ml 1 M hydrochloric acid and 20 ml water each time. The separated organic phase is dried over sodium sulfate. The solvent is removed by distillation. The oily residue is separated by column chromatography (silica gel: petroleum ether).

Yield 24 mmol

EXAMPLE 26

3-((E/Z)-)-6'-Chloro-2',2'-dimethyl-benzofuran-3'-ylidene)-androsta-1,4-diene-17-one-5'-yl-disodium phosphate A solution of 30 mmol 3-(androsta-1',4'-diene-17'-one-3'-ylidene)-6-chloro-5-hydroxy-2,2-dimethyl-benzofurane in a mixture of 30 ml acetone and 30 ml pyridine is added dropwise while stirring at 0° C. to a solution of 15 ml phosphoroxy chloride in 75 ml acetone. It is stirred for 1 hour at 0° C. and subsequently it is poured onto 600 ml saturated sodium chloride and suction filtered. The residue is suspended in 15 ml water. A pH value of 10 is set using 2 M sodium hydroxide solution. It is admixed with 300 ml ethanol and suction filtered. The residue is dried in a vacuum.

Yield 23 mmol

EXAMPLE 27

(4'Ξ)-5"-t.-Butyldimethylsilyloxy-6'-chloro-2",2"dimethyl-17-oxo-(3ξ)-dispiro[androsta-1,4-diene-3,3'-[1,2]dioxetane-4',3"-benzofurane 10 mmol 3-(androsta-1',4'-diene-17'-one-3'-ylidene)-6-chloro-5-t-butyldimethylsilyloxa-2,2-dimethyl-benzofurane dissolved in 20 ml absolute methylene chloride is irradiated for 2 hours at –30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 20 mmol

EXAMPLE 28

(4'Ξ)-6"-chloro-2",2"-dimethyl-17-oxo-(3ξO)-dispiro[androsta-1,4-diene-3,3'-[1,2]dioxetane-4',3"-benzofuran-5"-yl-disodium phosphate 2 mmol disodium salt of 3-(androsta-1',4'-diene-17'-one-3'-ylidene)-6-chloro-5-phosphoryl-2,2-dimethyl-benzofurane dissolved in 20 ml absolute methanol is irradiated for 8 hours at –30° C. with a 1000 watt sodium-vapour lamp in the presence of 0.01 mol % immobilized Rose Bengal while passing in dry oxygen. The reaction proceeds quantitatively. The sensitizer can be removed by filtration. The filtrate contains the dioxetane.

Yield 2 mmol

The corresponding dioxetanes based on the following benzofurane derivatives are prepared analogously to examples 1 to 28:
5-hydroxy-2,2-dimethyl-2,3-dihydro-benzofurane,
5-hydroxy-2,2-dimethyl-2,3-dihydro-benzofuran-3-one,
5-hydroxy-2,2-dimethyl-2,3-dihydro-benzofurane-3-thione,
6-chloro-5-hydroxy-2,2-dimethylbenzofuran-3-one and
6-chloro-5-hydroxy-2,2-dimethyl-benzofurane-3-thione.

What is claimed is:

1. A compound of formula (Ia) or (Ib)

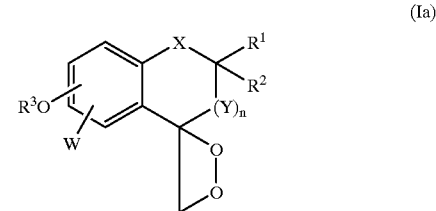

(Ia)

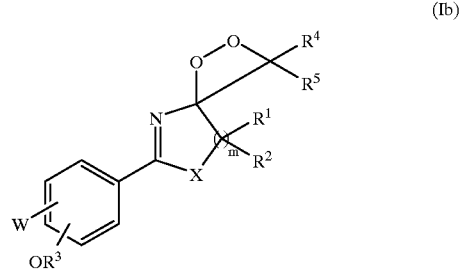

(Ib)

wherein
   $R^1$ and $R^2$ are each independently selected from the group consisting of hydrogen, straight-chained or branched $C_1$–$C_6$ alkyl, cycloalkyl and aryl, or $R^1$ and $R^2$ together form a cycloalkyl or aryl, with the proviso that at most one of $R^1$ and $R^2$ is hydrogen;

$R^3$ is a group which is capable of being cleaved off the O atom to which it is attached by an activating agent;

$R^4$ and $R^5$ are each independently hydrogen or a stabilizing group which protects the dioxetane group from uncontrolled conversion, or $R^4$ and $R^5$ together form a stabilizing group, with the proviso that at most one of $R^4$ and $R^5$ is hydrogen;

W is selected from the group consisting of hydrogen, halogen and pseudohalogen;

X and Y are each independently selected from the group consisting of a double bond, a carbonyl group, oxygen, N-R and $C(R)_2$, wherein R has the meanings of $R^1$ and $R^2$ above, m is 1 or 2; and n is 0 or 1.

2. The compound of claim 1, wherein the compound is selected from the group consisting of:

a compound of formula (Ia), wherein X is oxygen, n is 0 and O-$R^3$ is located on position 5 of the phenyl ring;

a compound of formula (Ib), wherein m is 1 and O-$R^3$ is located on position 3 of the phenyl ring; and a compound of formula (Ib), wherein m is 2 and O-$R^3$ is located on position 4 of the phenyl ring, wherein $R^1$–$R^5$, W and Y are as defined above.

3. The compound of claim 1, wherein O-$R^3$ is selected from the group consisting of a hydroxy salt, an oxy acid, a phosphate group, an arylcarboxylic ester, an alkylcarboxylic ester, an alkyloxy group, a trialkyloxy group, an alkylsilyloxy group, an arylsilyloxy group, a sulfate group, an oxypyranoside, a glyceridyl group and a phosphoryl group.

4. The compound of claim 1, wherein O-$R^3$ is a phosphate group or a dimethyl-tertiary butyl-silyloxy group.

5. The compound of claim 1, wherein $R^1$ and $R^2$ are each independently selected from the group consisting of hydrogen, methyl, ethyl and phenyl which is unsubstituted or substituted, or $R^1$ and $R^2$, together with the carbon atoms to which they are bound, form a phenylene group which is unsubstituted or substituted.

6. The compound of claim 1, wherein $R^4$ and $R^5$, together with the carbon atoms to which they are bound, form a condensed aliphatic or aromatic ring system which is unsubstituted or has at least one electron withdrawing group as a substitutent.

7. The compound of claim 6, wherein $R^4$ and $R^5$ are selected from the group consisting of adamantanyl group, phenyl group, cyclohexyl group, secondary or tertiary aliphatic alkyl group, polycycloalkyl group, polycycloaryl group, or a steroid derivative group, wherein any of the groups are unsubstituted or substituted with at least one electron withdrawing group.

8. The compound of claim 1, wherein the compound is of formula (Ia') or (Ia")

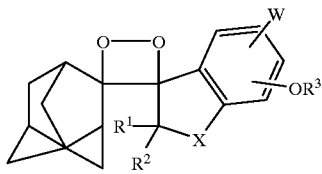

(Ia')

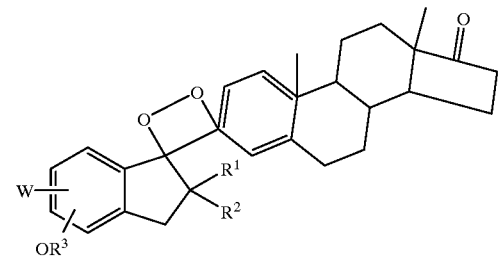

(Ia")

wherein $R^1$–$R^3$ and W are as defined above.

9. The compound of claim 8, wherein the compound is selected from the group consisting of:

3-(7'-t.-butyldimethylsilyloxy-2',2'-dimethyl-benzofuran-3'-yl)-4-spiro-(tricyclor3.3.1.1.$^{3,7}$]yl)-1,2-dioxetane, a disodium salt of 3-(7'-phosphoryl-2',2'-dimethyl-benzofuran-3'-yl)-4-spiro-(tricyclo [3.3.1.1.$^{3,7}$]yl)-1,2-dioxetane, 3-(7'-t.-butyl-dimethylsilyloxy-2',2'-dimethyl-benzofuran-3'-yl)-4-spiro-(5"-chloro-tricyclo [3.3.1.1.$^{3,7}$]yl)-1,2-dioxetane, a disodium salt of 3-(7'-phosphoryl-2',2'-dimethyl-benzofuran-3'-yl)-4-spiro-(5"-chloro-tricyclo [3.3.1.1.$^{3,7}$]-yl)-1,2-dioxetane, 3-(5'-t.-butyldimethylsilyloxy-2',2'-dimethyl-benzofuran-3'-yl)-4-spiro-(5"-chloro-tricyclo [3.3.1.1.$^{3,7}$]yl)-1,2-dioxetane, a disodium salt of 3-(5'-phosphoryl-2',2'-dimethyl-benzofuran-3'-yl)-4-spiro-(5"-chloro-tricyclo [3.3.1.1.$^{3,7}$]yl)-1,2-dioxetane, 3-(5'-t.-butyldimethylsilyloxy-6'-chloro-2',2'-dimethyl-benzofuran-3'-yl)-4-spiro-(5"-chloro-tricyclo [3.3.1.1.$^{3,7}$]yl)-1,2-dioxetane, a disodium salt of 3-(5'-phosphoryl-6'-chloro-2',2'-dimethyl-benzofuran-3'-yl)-4-spiro-(5"-chloro-tricyclo [3.3.1.1.$^{3,7}$]yl)-1,2-dioxetane, (4Ξ-)-5"-t.-butyldimethylsilyloxy-6"-chloro-2",2"-dimethyl-17-oxo-(3ζ)-dispiro[androsta-1,4-diene-3,3'-[1,2]dioxetane-4',3"-benzofurane and(4Ξ)-6"-chloro-2",2"-dimethyl-17-oxo-(3ξ)-dispiro[androsta-1,4-diene-3,3'-[1,2]dioxetane-4',3"-benzofuran-5"-yl-disodium phosphate.

10. A method for determining an analyte, comprising reacting the analyte with a compound as claimed in claim 1 to cleave the group $R^3$ therefrom to produce light from the reaction, and thereafter measuring the produced light to determined the analyte.

11. The method of claim 10, wherein the analyte is selected from the group consisting of an acid, a base, a salt, an enzyme, a DNA, an inorganic or organic catalyst and an electron donor.

12. The method of claim 10, wherein the analyte is an enzyme or a DNA.

13. The compound of claim 6 wherein at least one electron withdrawing group is a group with a positive $\delta_p$ value.

* * * * *